(12) United States Patent
Besset et al.

(10) Patent No.: US 11,634,664 B2
(45) Date of Patent: Apr. 25, 2023

(54) METHOD FOR PREPARING AN INVERSE EMULSION COMPRISING TWO CATIONIC POLYMERS

(71) Applicant: SNF GROUP, Andrezieux Boutheon (FR)

(72) Inventors: Céline Besset, Andrezieux Boutheon (FR); Frédéric Blondel, Andrezieux Boutheon (FR)

(73) Assignee: SNF GROUP, Andrezieux Boutheon (FR)

( * ) Notice: Subject to any disclaimer, the term of this patent is extended or adjusted under 35 U.S.C. 154(b) by 0 days.

(21) Appl. No.: 17/754,891

(22) PCT Filed: Oct. 23, 2020

(86) PCT No.: PCT/US2020/079870
§ 371 (c)(1),
(2) Date: Apr. 14, 2022

(87) PCT Pub. No.: WO2021/099060
PCT Pub. Date: May 27, 2021

(65) Prior Publication Data
US 2022/0348847 A1 Nov. 3, 2022

(30) Foreign Application Priority Data
Nov. 19, 2019 (FR) ....................... 1912918

(51) Int. Cl.
| | | |
|---|---|---|
| *A61K 8/06* | (2006.01) | |
| *A61K 8/81* | (2006.01) | |
| *C11D 3/37* | (2006.01) | |
| *C11D 11/00* | (2006.01) | |
| *C11D 3/00* | (2006.01) | |
| *C11D 17/00* | (2006.01) | |

(52) U.S. Cl.
CPC ............ *C11D 3/3773* (2013.01); *A61K 8/064* (2013.01); *A61K 8/8182* (2013.01); *C11D 3/0015* (2013.01); *C11D 3/3796* (2013.01); *C11D 11/0017* (2013.01); *C11D 17/0017* (2013.01)

(58) Field of Classification Search
CPC ...................................................... A61K 8/064
See application file for complete search history.

(56) References Cited

U.S. PATENT DOCUMENTS

| | | | |
|---|---|---|---|
| 8,633,278 B2 | 1/2014 | Broecher et al. | |
| 9,018,154 B2 * | 4/2015 | Blondel | C11D 3/001 510/506 |
| 2002/0188040 A1 | 12/2002 | Chen et al. | |

FOREIGN PATENT DOCUMENTS

| | | | | |
|---|---|---|---|---|
| EP | 0819651 A1 | 1/1988 | | |
| EP | 0262945 A2 | 4/1988 | | |
| FR | 2960548 A1 * | 12/2011 | ............ | C08F 220/34 |
| FR | 3024736 A1 * | 2/2016 | ......... | C11D 17/0008 |
| GB | 845573 A | 8/1960 | | |

OTHER PUBLICATIONS

International Search Report (and English Translation) and Written Opinion for PCT/EP2020/079870, dated Mar. 12, 2021.

* cited by examiner

*Primary Examiner* — Gina C Justice
(74) *Attorney, Agent, or Firm* — Heslin Rothenberg Farley & Mesiti P.C.

(57) ABSTRACT

This invention relates to a process for preparing an inverse emulsion comprising mixing an aqueous solution comprising a water-soluble (co)polymer A synthesized from at least one cationic monomer and an inverse EMI 2 emulsion comprising a water-soluble (co)polymer B synthesized from at least one cationic monomer, optionally followed by distillation.

This invention also relates to the inverse emulsion thus obtained, a detergent or cosmetic or softening composition comprising such an inverse emulsion, as well as the use of such an inverse emulsion to improve the softening properties of a fabric softening composition.

17 Claims, 3 Drawing Sheets

METHOD FOR PREPARING AN INVERSE EMULSION COMPRISING TWO CATIONIC POLYMERS

CROSS REFERENCE TO RELATED APPLICATIONS

This application is a national stage filing under section 371 of International Application No. PCT/EP2020/079870, filed on Oct. 23, 2020, and published on May 27, 2021 as WO 2021/099060, which claims priority to French Application No. 1912918, filed on Nov. 19, 2019. The entire contents of WO 2021/099060 are hereby incorporated herein by reference.

TECHNICAL FIELD OF THE INVENTION

This invention relates to a process for the preparation of an inverse emulsion comprising two (co)polymers. The process according to the invention makes it possible to obtain an inverse emulsion that is easy to handle and makes it possible to benefit the consumer in the field of products for detergents and cosmetics (referred to as "Home and Personal Care").

PRIOR ART

At least two polymers, each with a cationic charge, are often used in detergent or cosmetic formulations. These polymers may serve as a thickener, aid in the deposition of active ingredients, or even be used for their conditioning properties (improvement in softness and reduction in static adhesion). These polymers often have high molecular masses and have a high apparent viscosity in solution in water.

One problem encountered by formulators is that when two or more cationic polymers are used in the formulation of these compositions, they are often incompatible with each other. Because these polymers are used for different purposes, they generally do not have the same chemistry, which leads to a certain degree of incompatibility. Direct mixing of such cationic polymers, prepared independently of each other by polymerization of monomers, is therefore not homogeneous.

Depending on the type of polymerization, dephasing, flocculation, or precipitation phenomena may be observed. Therefore, the incorporation of these polymers into the composition formulations must be done separately.

The formulator also experiences difficulties in the implementation of these polymers, whether it is for the unloading, storage, and dosing of these polymers in formulations often manufactured in a continuous process.

Document EP 0 262 945 describes the formation of a homogeneous mixture of two water-soluble polymers, prepared according to a specific process comprising the formation of a first polymer by polymerization of its starting monomers in an aqueous solution containing a second polymer prepared beforehand. This mixture of polymers finds applications in the manufacture of paper or in the treatment of drinking or mining water, or even as a color fixer in textiles.

Document U.S. Pat. No. 8,633,278 describes a bimolecular inverse emulsion of cationic polymers, where the monomers of the second cationic polymer are polymerized in the presence of a first cationic polymer. The inventors observe a synergistic effect only obtained by the polymerization of the second cationic polymer in the presence of a first cationic polymer, making better performance possible from the polymers in paper manufacturing or water treatment.

US 2002/0188040 describes a water-soluble polymer complex obtained from a first water-soluble polymer and one or more water-soluble monomers polymerized in the presence of the first polymer. The complex thus obtained is soluble in water and does not contain particles of insoluble polymers. This complex may be used for water treatment, paper manufacturing, or as a rheological modifier when added to an aqueous solution, especially for applications in the manufacture of ink, paint, or adhesive.

Documents EP 0 262 945, U.S. Pat. No. 8,633,278 and US2002/0188040 do not describe polymer blends. On the contrary, document U.S. Pat. No. 8,633,278 specifies that a synergistic effect is obtained thanks to a bimolecular polymer system.

Document GB 845,573 describes an aqueous dispersion of polyamide and its use for covering surfaces (wood, metal, paper, textile, etc.). This dispersion is prepared by forming a clear and oil- and water-impermeable film after drying. It is not an emulsion, let alone an inverse emulsion, containing water-soluble polymers.

Document EP 0 819 651 describes a composition for dewatering sludge, obtained (i) by forming an aqueous solution of non-ionic monomers, cationic monomers, and a cationic polymer, the whole being soluble in water, (ii) emulsifying the aqueous solution in a sufficient amount of hydrocarbon oil to form a water-in-oil emulsion, and (iii) polymerizing the monomers.

Be that as it may, there is a need to obtain stable polymer mixtures and to facilitate the handling of these viscous and difficult-to-handle products used for detergent and cosmetic compositions while retaining the unaltered properties of these polymers.

The Applicant has discovered, surprisingly, that the process according to the invention makes it possible, in addition to meeting the current needs of formulators (facilitating the handling of viscous polymers), to obtain polymers offering better performance than if they are separately added to the detergent or cosmetic composition.

DISCLOSURE OF THE INVENTION

This invention relates to a process for preparing an inverse EMI 1 emulsion comprising the following step:

Forming an inverse EMI 1 emulsion by mixing an aqueous solution of water-soluble (co)polymer A with at least one cationic monomer and an inverse EMI 2 emulsion of water-soluble (co)polymer B of at least one cationic monomer.

Another subject-matter of the invention relates to a detergent or cosmetic or fabric softener composition, comprising an inverse emulsion (EMI 1 or EMI 3) obtained by the process according to the invention.

Another subject-matter of the invention relates to the use of an inverse emulsion (EMI 1 or EMI 3) obtained by the process according to the invention for improving the softening properties of a fabric softening composition.

Also part of the invention are all the possible combinations of the various embodiments disclosed, whether they are preferred embodiments or given by way of example. In addition, when value ranges are indicated, the limits make up part of these ranges. The disclosure also includes all combinations between the limits of these value ranges. For example, the ranges of values "1-20, preferably 5-15" imply the disclosure of the ranges 1-5, 1-15, 5-20, and 15-20.

This invention makes it possible to reduce the viscosity of a composition of (co)polymers compared to an aqueous solution containing the same quantity of these (co)polymers. Therefore, this invention facilitates the use of viscous (co) polymers, particularly in terms of transporting these (co) polymers in a pipeline or maintaining these pipelines. In addition, the reduction in viscosity results in energy savings, as the transport of (co)polymers is facilitated, and less powerful pumps are required. The process according to the invention is also easier to implement than the formation of a (co)polymer by polymerization of monomers in the presence of another (co)polymer.

Water-Soluble (Co)Polymers A and B

The term "(co)polymer" designates a homopolymer or a copolymer.

Water-soluble (co)polymers A and B may be different or identical, but their shape is different.

Indeed, water-soluble (co)polymer A is in the form of an aqueous solution, while water-soluble (co)polymer B is in the form of an inverse water-in-oil emulsion. (Co)polymer A is preferably different from water-soluble (co)polymer B. More specifically, while different, water-soluble (co)polymers A and B do not have the same monomeric composition and/or the same molar mass.

Preferably, water-soluble (co)polymers A and B are two distinct (co)polymers.

Water-soluble (co)polymer means a (co)polymer that gives an aqueous solution without insoluble particles when dissolved while stirring at 25° C. and at a concentration of 10 g·l$^{-1}$ in water.

(Co)polymers A and B being water-soluble, they are in the aqueous phase of the inverse emulsions EMI 1 and EMI 3.

Water-soluble (co)polymers A and B may be synthetic or semi-synthetic (co)polymers. Preferably, water-soluble (co) polymers A and B are synthetic (co)polymers.

Semi-synthetic (co)polymers are to be understood as a natural (co)polymer that has undergone chemical grafting reactions with various synthetic substituents. Those skilled in the art are familiar with this kind of reaction which remains conventional chemical reactions applied to natural polymers.

The water-soluble (co)polymers A and B are (co)polymers obtained, independently of each other, from at least one cationic monomer and optionally from at least one non-ionic monomer and/or at least one anionic monomer.

According to the invention, the phrase "A and/or B" should be understood as "A, or B, or A and B".

According to the invention, the phrase "independently of each other" should be understood to mean that the preparation of one of these (co)polymers is performed independently of the preparation of the other of these (co)polymers.

The cationic monomer(s) which may be used in the context of the invention are preferably chosen from, in particular, vinyl monomers, more particularly from the acrylamide, acrylic, allylic or maleic type possessing a quaternary ammonium function. Mention may be made, in particular and without limitation, of quaternized dimethylaminoethyl acrylate (ADAME), quaternized dimethylaminoethyl methacrylate (MADAME), dimethyldiallylammonium chloride (DADMAC), acrylamido propyltrimethyl ammonium chloride (APTAC), methacrylamido propyltrimethyl ammonium chloride (MAPTAC), and mixtures thereof.

A person skilled in the art will know how to prepare the quaternized monomers, for example, by means of alkyl halide of the R—X type, R being an alkyl group, and X being a halogen (in particular methyl chloride). Furthermore, this invention also covers monomers of the DADMAC, APTAC, and MAPTAC type, the halide counterion of which is fluoride, bromide, or iodide instead of chloride.

Preferably, the cationic monomer(s) which may be used in the context of the invention are chosen from quaternized dimethylaminoethyl acrylate (ADAME), quaternized dimethylaminoethyl methacrylate (MADAME), dimethyldiallylammonium chloride (DADMAC), acrylamido propyltrimethyl ammonium chloride (APTAC), methacrylamido propyltrimethyl ammonium chloride (MAPTAC), and mixtures thereof.

More preferably, the cationic monomer used to form water-soluble (co)polymer A is dimethyldiallylammonium chloride (DADMAC).

More preferably, the cationic monomer used to form water-soluble (co)polymer B is quaternized dimethylaminoethyl methacrylate (MADAME).

Advantageously, the cationic monomer content used to form water-soluble (co)polymer A is between 1 and 100% by weight, relative to the total mass of monomers constituting water-soluble (co)polymer A. Thus, it may be at least 2% mass, for example, at least 5% mass, for example, at least 10% by weight, for example, at least 15% by weight, for example, at least 20% by weight, for example, at least 30% by weight, for example, at least 40% by weight, for example, at least 50% by weight. Preferably, it is less than or equal to 99% by weight, for example, less than or equal to 98% by weight, for example, less than or equal to 95% by weight, for example, less than or equal to 90% by weight, for example, less than or equal to 85% by weight, for example, less than or equal to 80% by weight, for example, less than or equal to 70% by weight, for example, less than or equal to 60% by weight.

Advantageously, the cationic monomer content used to form water-soluble (co)polymer B is between 1 and 100% by weight relative to the total mass of monomers constituting water-soluble (co)polymer B. Preferably, it is at least 2% by weight, for example, at least 5% by weight, for example, at least 10% by weight, for example, at least 15% by weight, for example, at least 20% by weight, for example, at least 30% by weight, for example, at least 40% by weight, for example, at least 50% by weight. Preferably, it is less than or equal to 99% by weight, for example, less than or equal to 98% by weight, for example, less than or equal to 95% by weight, for example, less than or equal to 90% by weight, for example, less than or equal to 85% by weight, for example, less than or equal to 80% by weight, for example, less than or equal to 70% by weight, for example, less than or equal to 60% by weight.

The non-ionic monomer(s) that may be used in the context of the invention is (are) generally chosen from water-soluble vinyl monomers. Preferred monomers belonging to this family are, for example, acrylamide, methacrylamide, N-isopropylacrylamide, N,N-dimethylacrylamide, N-methylolacrylamide, N-vinylformamide, N-vinyl acetamide, N-vinylpyridine, N-vinylpyrrolidone, acryloyl morpholine (ACMO), diacetone acrylamide, and mixtures thereof.

Preferably, the non-ionic monomer(s) that may be used in the context of the invention are chosen from methacrylamide and acrylamide, even more preferably acrylamide.

Advantageously, the non-ionic monomer content used to form water-soluble (co)polymer A is between 0 and 99% by weight based on the total weight of monomers constituting water-soluble (co)polymer A. Preferably, it is at least 1% by weight, for example, at least 2% by weight, for example, at least 5% by weight, for example, at least 10% by weight, for example, at least 15% by weight, for example, at least 20% by weight, for example, at least 30% by weight, for example, at least 40% by weight, for example, at least 50% by weight. Preferably, it is less than or equal to 98% by weight, for example, less than or equal to 95% by weight, for example, less than or equal to 90% by weight, for example, less than or equal to 85% by weight, for example, less than or equal to 80% by weight, for example, less than or equal to 70% by weight, for example, less than or equal to 60% by weight.

According to the invention, reference is made to monomer(s) constituting a (co)polymer and not to a monomeric unit (which is the building block constituting the (co)polymer) for the sake of clarity. As is known to those skilled in the art, the monomeric unit comes directly from the monomer by polymeric reaction. The monomer is, therefore, either the starting compound for the polymerization or the unit present in the (co)polymer.

Advantageously, the non-ionic monomer content used to form water-soluble (co)polymer B is between 0 and 99% by weight based on the total weight of monomers constituting water-soluble (co)polymer B. Preferably, it is at least 1% by weight, for example, at least 2% by weight, for example, at least 5% by weight, for example, at least 10% by weight, for example, at least 15% by weight, for example, at least 20% by weight, for example, at least 30% by weight, for example, at least 40% by weight, for example, at least 50% by weight. Preferably, it is less than or equal to 98% by weight, for example, less than or equal to 95% by weight, for example, less than or equal to 90% by weight, for example, less than or equal to 85% by weight, for example, less than or equal to 80% by weight, for example, less than or equal to 70% by weight, for example, less than or equal to 60% by weight.

The amounts of monomer(s) will be adjusted by those skilled in the art so as not to exceed 100% by weight during the preparation of water-soluble (co)polymers according to the invention.

The anionic monomer(s) which may be used in the context of the invention are preferably chosen from acrylic acid, methacrylic acid, itaconic acid, maleic acid, sulfonated derivatives of (meth)acrylic acid, for example, 2-acrylamido-2-methylpropane sulfonic acid (ATBS), vinylsulfonic acid, vinylphosphonic acid, and mixtures thereof, said anionic monomer being non-salified, partially or totally salified, and the salts of the methacrylate of 3-sulpropyl.

The salified form advantageously corresponds to salts of alkali metals (Li, Na, K, etc.), alkaline-earth metals (Ca, Mg, etc.), or ammonium, in particular, quaternary ammoniums. Preferred salts are sodium salts. The non-salified form corresponds to the acid form of the anionic monomer, for example, $CH_2=CH-C(=O)OH$ in the case of acrylic acid.

Preferably, the anionic monomer(s) which may be used in the context of the invention are chosen from (meth)acrylic acid, 2-acrylamido-2-methylpropanesulfonic acid (ATBS), said anionic monomer being non-salified, partially, or totally salified. Even more preferably, the anionic monomer used in the context of the invention is unsalified, partially, or totally salified acrylic acid. Advantageously, the anionic monomer content used to form water-soluble (co)polymer A is between 0 and 99% by weight with respect to the total mass of monomers constituting water-soluble (co)polymer A. Preferably, it is at least 1% by weight, for example, at least 2% by weight, for example, at least 5% by weight, for example, at least 10% by weight, for example, at least 15% by weight, for example, at least 20% by weight, for example, at least 30% by weight, for example, at least 40% by weight, for example, at least 50% by weight. Preferably, it is less than or equal to 98% by weight, for example, less than or equal to 95% by weight, for example, less than or equal to 90% by weight, for example, less than or equal to 85% by weight, for example, less than or equal to 80% by weight, for example, less than or equal to 70% by weight, for example, less than or equal to 60% by weight.

Advantageously, the anionic monomer content used to form water-soluble (co)polymer B is between 0 and 99% by weight based on the total weight of monomers constituting water-soluble (co)polymer B. Preferably, it is at least 1% by weight, for example, at least 2% by weight, for example, at least 5% by weight, for example, at least 10% by weight, for example, at least 15% by weight, for example, at least 20% by weight, for example, at least 30% by weight, for example, at least 40% by weight, for example, at least 50% by weight. Preferably, it is less than or equal to 98% by weight, for example, less than or equal to 95% by weight, for example, less than or equal to 90% by weight, for example, less than or equal to 85% by weight, for example, less than or equal to 80% by weight, for example, less than or equal to 70% by weight, for example, less than or equal to 60% by weight.

The amounts of monomer(s) will be adjusted by those skilled in the art so as not to exceed 100% by weight during the preparation of water-soluble (co)polymers according to the invention.

According to one particular embodiment, the anionic nature of water-soluble (co)polymers A and B may be obtained by post hydrolysis. Post hydrolysis corresponds to a reaction of the (co)polymer after its formation by polymerization of the monomers. This step consists of the reaction of hydrolyzable functional groups of monomers, advantageously of non-ionic monomers, more advantageously of monomers containing a hydrolyzable amide or ester function, with a hydrolysis agent. This hydrolysis agent may, in particular, be an enzyme, an ion exchange resin, or an alkali metal. Preferably, the hydrolysis agent is a Bronsted base, for example, NaOH or KOH. During this step of post-hydrolysis of the (co)polymer, the number of carboxylic acid functions increases.

Indeed, the reaction between the base and the amide or ester functions present in the (co)polymer produces carboxylate groups. The hydrolysis may be partial or total.

According to certain embodiments, in addition to the monomers above, water-soluble (co)polymers A and B may also comprise one or more hydrophobic monomers chosen, in particular, from vinyl monomers, more particularly of the acrylamide, acrylic, allylic, or maleic acid with a pendent hydrophobic function. These hydrophobic monomers are preferably chosen from acrylamide derivatives such as N-alkylacrylamides, for example, diacetone acrylamide, N-tert-butylacrylamide, octylacrylamide; N,N-dialkylacrylamides such as N,N-dihexylacrylamide; and acrylic acid derivatives such as alkyl acrylates and methacrylates and mixtures thereof. Preferably, they are chosen from esters of (meth)acrylic acid having an alkyl, arylalkyl, propoxylated, ethoxylated, or ethoxylated and propoxylated chain; (meth)acrylamide derivatives with an alkyl, arylalkyl propoxylated, ethoxylated, ethoxylated and propoxylated, or dialkyl chain; alkyl aryl sulfonates. The alkyl, aryl, and alkyl aryl groups are advantageously and independently of one another, hydrocarbon groups comprising between 1 and 10 carbon atoms.

Advantageously, the (co)polymers A and B comprise, independently of each other, less than 10% by weight of hydrophobic monomer with respect to the total weight of monomers constituting the water-soluble (co)polymer A or B, more advantageously between 0.01 and 5% mass.

When (co)polymers A and B comprise hydrophobic monomers, those skilled in the art will know how to adjust the amounts of the various monomers in order to obtain the desired properties while maintaining the water solubility of the (co)polymers.

Monomers having a zwitterionic character may also be used in the invention. The zwitterionic monomer may be a derivative of a unit of the vinyl type, advantageously acrylamide, acrylic, allylic or maleic possessing an amine or quaternary ammonium function and an acid function of the carboxylic (or carboxylate), sulfonic (or sulfonate) or phosphoric type (or phosphate). Mention may be made, in particular and without limitation, of derivatives of dimethylaminoethyl acrylate, such as 2-((2-(acryloyloxy)ethyl)dimethylammonio)ethane-1-sulfonate, 3-((2-(acryloyloxy)ethyl) dimethylammonio) propane-1-sulfonate, 4-((2-(acryloyloxy)ethyl) dimethylammonio) butane-1-sulfonate, [2-(acryloyloxy)ethyl](dimethylammonio) acetate, derivatives of dimethylaminoethyl methacrylate such as 2-((2-(methacryloyloxy)ethyl)dimethylammonio)ethane-1-sulfonate, 3-((2-(methacryloyloxy)ethyl)dimethylammonio) propane-1-sulfonate, 4-((2-(methacryloyloxy)ethyl) dimethylammonio)butane-1-sulfonate, [2-(methacryloyloxy)ethyl)](dimethylammonio) acetate, derivatives of dimethylamino propylacrylamide such as 2-((3-acrylamidopropyl) dimethylammonio) ethane-1-sulfonate, 3-((3-acrylamidopropyl) dimethylammonio) propane-1-sulfonate, 4-((3-acrylamidopropyl) dimethylammonio) butane-1-sulfonate, the [3-(acryloyloxy) propyl] (dimethylammonio) acetate, derivatives of dimethylamino propyl methylacrylamide such as 2-((3-methacrylamidopropyl) dimethylammonio) ethane-1-sulfonate, 3-((3-methacrylamidopropyl) dimethylammonio) propane-1-sulfonate, 4-((3-methacrylamidopropyl) dimethylammonio) butane-1-sulfonate and [3-(methacryloyloxy)propyl](dimethylammonio) ethylammonio) acetate.

According to one preferred embodiment of the invention, water-soluble (co)polymer A is a water-soluble (co)polymer synthesized from at least one cationic monomer and at least one anionic monomer water-soluble (co)polymer A having an overall cationic charge.

According to one preferred embodiment of the invention, water-soluble (co)polymer B is a cross-linked water-soluble (co)polymer.

According to one particular embodiment of the invention, water-soluble (co)polymers A and B have, independently of each other, a mass-average molar mass of between 50,000 g/mol and 5,000,000 g/mol, preferably between 100,000 g/mol and 3,000,000 g/mol.

The mass-average molar mass is advantageously determined by high-performance liquid chromatography (often known by its acronym HPLC for "high-performance liquid chromatography"), for example, by means of the following instruments and protocol:

*Chromatographic System: Agilent 1260 liquid chromatography or equivalent

*Detectors:

Dual-wavelength UV 1260 or equivalent

Wyatt Dawn Heleos II: 18-angle light scattering (MALS)

Wyatt ViscoStar II: viscometer

Wyatt T-Rex or equivalent: Refractive index

*Chromatographic columns:

Shodex OHpak SB-807 HQ*35 μm

Shodex OHpak SB-805 HQ*13 μm

Shodex OHpak SB-803 HQ*6 μm

Shodex OHpak SB-802 HQ*8 μm

*Method:

Temperature: 25° C.

Mobile phase: 0.4M $NaNO_3$+100 ppm $NaN_3$, TFA 0.05% (pH=3.5)

Injection: 100 μL

Flow rate: 0.5 ml/min—Detection: Dawn HELEOS (MALS), Optilab T-Rex (RI)

In general, the formation of water-soluble (co)polymer A does not require any particular polymerization process. It may be obtained by all the polymerization techniques well known to those skilled in the art resulting in a (co)polymer advantageously in powder form: gel polymerization followed by drying and grinding steps; precipitation polymerization; polymerization in solution, followed by a drying step, advantageously by spraying (or "spray drying"); reverse suspension polymerization, advantageously for obtaining microbeads; micellar polymerization whether or not followed by a precipitation step; post-hydrolysis or co-hydrolysis polymerization; so-called "template" polymerization, radical, or even controlled radical, and more particularly of the RAFT type (acronym for "Reversible Addition Fragmentation Chain Transfer").

The polymerization is generally a free radical polymerization. According to the invention, "polymerization by free radicals" should be understood to mean a polymerization by free radicals by means of at least one UV, azo, redox, or thermal initiator or else a technique of controlled radical polymerization (CRP) or else a technique of matrix polymerization.

Preferably, water-soluble (co)polymer A is obtained by a solution polymerization process.

Preferably, the concentration of water-soluble (co)polymer A of the aqueous solution when it is mixed with EMI 2 according to the process of the invention is between 1 and 70% mass. Preferably, it is at least 1% mass, for example, at least 2% mass, for example, at least 3% mass, for example, at least 5% mass, for example, at least 10% by weight, for example, at least 15% by weight, for example, at least 20% by weight, for example, at least 30% by weight. Preferably, it is less than or equal to 65% by weight, for example, less than or equal to 60% by weight, for example, less than or equal to 55% by weight, for example, less than or equal to 50% by weight, for example, less than or equal to 40% by weight.

According to one particular embodiment of the invention, prior to the formation of the aqueous solution implemented in the process, water-soluble (co)polymer A may be in liquid, gel, or solid form.

Preferably, water-soluble (co)polymer B is obtained by an inverse emulsion polymerization process (water in oil). Such a method is known to those skilled in the art. The expression "inverse emulsion" denotes both inverse emulsions and inverse microemulsions.

Generally, an aqueous solution comprising the monomer(s) and the emulsifying agent(s) is emulsified in an oily phase. Then, the polymerization is carried out by adding a free radical initiator. Reference may be made to redox couples, with cumene hydroperoxide, tertiary butylhydroxyperoxide, or persulfates among the oxidizing agents, sodium sulfite, sodium metabisulfite, and Mohr's salt among the reducing agents. Azo compounds such as 2,2'-azobis (isobutyronitrile) and 2,2'-azobis (2-amidinopropane) hydrochloride may also be used.

Conventionally, the polymerization is generally carried out in an isothermal, adiabatic, or temperature-controlled manner. That is to say that the temperature is kept constant, generally between 10° C. and 60° C. (isothermal); or the temperature is allowed to increase naturally (adiabatic), and in this case, the reaction is generally started at a temperature below 10° C., and the final temperature is generally above 50° C.; or, finally, the temperature increase is controlled so as to have a temperature curve between the isothermal curve and the adiabatic curve.

The oil used to prepare the inverse EMI 2 emulsion comprising water-soluble (co)polymer B may be a mineral oil, a vegetable oil, a synthetic oil, or a mixture of several of these oils. Examples of mineral oil are mineral oils containing saturated hydrocarbons of the aliphatic, naphthenic, paraffinic, isoparaffinic, cycloparaffinic, or naphthyl type. Examples of synthetic oil are hydrogenated polydecene or hydrogenated polyisobutene, an ester such as octyl stearate, or butyl oleate. Exxon's Exxsol® product line is a perfect fit.

In general, the mass ratio of the water phase to the oil phase during the polymerization is preferably between 50/50 and 90/10, more preferentially between 70/30 and 80/20.

According to this invention, the term "emulsifying agent" denotes an agent capable of emulsifying water in an oil, and an "inverting agent" is an agent capable of emulsifying an oil in water.

Specifically, an inverting agent is considered to be a surfactant with a hydrophilic-lipophilic balance (HLB) greater than or equal to 10, and an emulsifying agent is a surfactant with an HLB strictly less than 10.

The hydrophilic-lipophilic balance (HLB) of a chemical compound is a measure of its degree of hydrophilicity or lipophilicity, determined by calculating the values of different regions of the molecule, as described by Griffin in 1949 (Griffin W C, *Classification of Surface Active Agents by HLB*, Journal of the Society of Cosmetic Chemists, 1949, 1, pages 311-326).

According to this invention, we have adopted Griffin's method of calculating a value based on the chemical groups of the molecule. Griffin assigned a dimensionless number between 0 and 20 to give information on water and oil solubility. Substances with an HLB value of 10 are distributed between the two phases so that the hydrophilic group (molecular weight Mh) is completely projected into the water while the hydrophobic hydrocarbon group (molecular weight Mp) is adsorbed in the non-aqueous phase.

The HLB value of a substance with a total molecular weight of M, a hydrophilic part of molecular weight Mh, and a hydrophobic part with a molecular weight of Mp is calculated as: HLB=20 (Mh/Mp).

Examples of reversing agents are ethoxylated sorbitan esters such as ethoxylated sorbitan oleate with 20 equivalents of ethylene oxide (EO 20), polyethoxylated sorbitan laurate with 20 equivalents of ethylene oxide, castor oil polyethoxylated, oleodecyl alcohol decaethoxylated, lauryl alcohol heptamethoxylated, and sorbitan polyethoxy monostearate with 20 equivalents of ethylene oxide. The reversing agent may also be polyoxyethylene alkylphenol; polyoxyethylene (10 equivalents of ethylene oxide) cetyl ether; polyoxyethylene alkyl-aryl ether; quaternary ammonium derivatives; potassium oleate; N-cetyl-N-ethyl morpholinium ethosulfate; sodium lauryl sulphate; condensation products of higher fatty alcohols with ethylene oxide, such as the reaction product of oleyl alcohol and 10 equivalents of ethylene oxide; condensation products of alkylphenols and ethylene oxide, such as the reaction products of isooctylphenol with 12 equivalents of ethylene oxide; condensation products of higher fatty acid amines with five or more equivalents of ethylene oxide; ethylene tristerylphenol oxide; ethylene oxide condensation products of polyol partially higher fatty esters, and their internal anhydrides (e.g., mannitol anhydride and sorbitol anhydride); amine oxides; alkylpolyglucosides; glucamides; phosphate esters or salts of alkylbenzene sulfonic acids; or surfactant water-soluble polymers.

Preferably, the inverting agent is an ethoxylated nonylphenol, preferably with an ethoxylation of 4 to 10, or an ethoxylated/propoxylated alcohol, preferably with a C12 to C25 ethoxylation/propoxylation, or ethoxylated tridecyl alcohol, or an ethoxy/propoxylated fatty alcohol. Advantageously, the ethoxylation corresponds to 2 to 5 ethoxy units while the ethoxylation/propoxylation is advantageously C12-C15.

The water-in-oil emulsion comprises between 1 and 10% by weight of at least one reversing agent, preferably between 3 to 7% mass.

Preferably, the concentration of water-soluble (co)polymer B in the inverse EMI 2 emulsion is between 5 and 50% mass. Preferably, it is at least 5% mass, for example, at least 7% mass, for example, at least 10% by weight, for example, at least 15% by weight, for example, at least 20% by weight, for example, at least 25% by weight. Preferably, it is less than or equal to 50% by weight, for example, less than or equal to 45% by weight, for example, less than or equal to 40% by weight, for example, less than or equal to 35% by weight, for example, less than or equal to 30% by weight.

According to one particular embodiment, water-soluble (co)polymer A has an amphoteric character (cationic and anionic charges), that is to say, that it is prepared from at least one cationic monomer and at least one anionic monomer or at least one non-ionic monomer undergoing a post-hydrolysis reaction, and optionally at least one other non-ionic monomer. The monomers constituting water-soluble (co)polymer A are preferably chosen from the lists described above.

The overall charge of water-soluble (co)polymer A is preferentially cationic. Thus, the mass ratio between cationic monomers and anionic monomers in water-soluble (co)polymer A is preferably greater than 1. Preferably, the mass ratio between cationic monomers and anionic monomers in water-soluble (co)polymer A is between 1 and 100, more preferably between 2 and 50, more preferably between 4 and 30, and more preferably between 6 and 20.

According to one preferred embodiment, water-soluble (co)polymer A is a (co)polymer of non-salified acrylic acid, partially or totally salified, and of dimethyldiallylammonium chloride (DADMAC).

Preferably, in water-soluble (co)polymer A, the mass ratio between dimethyldiallylammonium chloride (DADMAC) and non-salified acrylic acid, partially or totally salified, is between 1 and 100, more preferably between 2 and 50, and even more preferably between 4 and 30. According to one particular embodiment of the invention, water-soluble (co)polymer B is a cross-linked water-soluble (co)polymer.

The cross-linking agent(s) which may be used within the context of the invention are advantageously chosen from polyethylenically unsaturated monomers having at least two unsaturated functions, such as vinyl and epoxy functions. These may include CH=CH functions (possibly substituted), allylic functions, or acrylic functions. Examples include methylene bis acrylamide (MBA), triallyamine, or macroinitiators such as polyperoxides, polyazoids, and polytransfer agents such as polymercaptan (co)polymers.

Preferably, the amount of cross-linking agent is between 0.001 and 0.15% mass relative to the total mass of monomers constituting water-soluble (co)polymer B. More preferably, it is between 0.01 and 0.1% mass.

According to one preferred embodiment of the invention, water-soluble (co)polymer B is a (co)polymer of acrylamide and dimethylaminoethyl methacrylate (MADAME) quaternized (advantageously with $CH_3Cl$).

Preferably, the mass ratio between quaternized dimethylaminoethyl methacrylate (MADAME) (advantageously with $CH_3Cl$) and acrylamide is greater than 0 and less than or equal to 30, more preferably between 5 and 20, and even more preferably between 10 and 15.

Even when cross-linked, water-soluble (co)polymer B remains water-soluble. A person skilled in the art will know how to adjust the quantity of cross-linking agents and optionally of the transfer agent in order to achieve this result.

According to one particular embodiment of the invention, the overall charge of water-soluble (co)polymers A and B is preferentially cationic.

Description of the Process for Obtaining the Inverse EMI 1 Emulsion

The process, according to the invention, consists of properly mixing an aqueous solution of a water-soluble (co)polymer A with an inverse EMI 2 emulsion of a water-soluble (co)polymer B.

In general, the mass ratio of the water phase to the oil phase of the inverse EMI 1 emulsion is preferably between 1 and 6, more preferably between 2 and 4.

The new inverse EMI 1 emulsion formed by mixing the aqueous solution of water-soluble (co)polymer A and the inverse emulsion of water-soluble (co)polymer B generally does not require any supplemental addition of surfactant. However, it is possible to add more. Furthermore, it is also conceivable to add an inverter, in particular, if the EMI 1 emulsion does not contain one.

Mixing is preferably done by adding the aqueous solution of water-soluble (co)polymer A to the inverse EMI 2 emulsion of water-soluble (co)polymer B. But mixing may also be done by adding the emulsion reverse EMI 2 of water-soluble (co)polymer B in the aqueous solution of water-soluble (co)polymer A. It may also be carried out by simultaneous introduction of the aqueous solution of water-soluble (co)polymer A and the reverse EMI 2 emulsion into the same container.

The addition (or mixing) of the aqueous solution comprising water-soluble (co)polymer A in the inverse EMI 2 emulsion of (co)polymer B may be done all at once, or it may be done several times (at least twice). This may be done continuously.

Mixing the solution of water-soluble (co)polymer A with the inverse EMI 2 emulsion of water-soluble (co)polymer B may be done by any means known to those skilled in the art. For example, and in a non-exhaustive way, it may be carried out by agitation using a magnetic bar, an agitation blade, or a double agitation blade. It is preferable to use a stirring blade for stirring.

The stirring time of the mixture is generally between 2 minutes and 60 minutes, preferably it is between 5 minutes and 30 minutes, more preferably between 10 minutes and 20 minutes. The stirring speed of the mixture is preferably between 10 rpm and 1000 rpm (rpm=rotation per minute), more preferably between 100 rpm and 800 rpm, and even more preferably between 400 rpm and 600 rpm. In general, too little stirring will not prevent the formation of a new EMI 1 reverse emulsion, while too much stirring may break the EMI 2 reverse emulsion and/or the EMI 1 emulsion.

Advantageously, the stirring temperature should be between 15° C. and 65° C. This temperature is advantageously adjusted according to the nature of (co)polymers A and B. At too high or too low a temperature, depending on the cationicity of the (co)polymer, compatibility problems may be encountered between (co)polymers A and B comprising cationic monomers, resulting in the precipitation of part of (co)polymers A and B. Those skilled in the art will know how to adapt this temperature in order to obtain a satisfactory mixture, without precipitation, that is, without the formation of insoluble particles at 25° C.

In one particular embodiment, the mass ratio between water-soluble (co)polymer B and water-soluble (co)polymer A in the inverse EMI 1 emulsion or EMI 3 is between 1 and 100. Preferably, it is between 2 and 70, more preferably between 3 and 50, even more preferably between 4 and 30, and even more preferably between 5 and 14.

According to one particular embodiment of the invention, the total concentration of water-soluble (co)polymers A and B in the inverse EMI 1 emulsion is between 5 and 50% by weight relative to the total mass of the inverse EMI 1 emulsion. Preferably, it is between 10 and 40% by weight, more preferably it is between 15 and 35% by weight, and more preferably between 20 and 30% by weight.

A person skilled in the art will know how to adapt the concentrations of water-soluble (co)polymer A, and of water-soluble (co)polymer B (in the EMI 2 emulsion) so as to obtain the concentrations of water-soluble (co)polymers A and B desired in the EMI 1 emulsion according to the invention.

One particular embodiment of the invention relates to a method for preparing an inverse EMI 1 emulsion comprising mixing an aqueous solution comprising a water-soluble (co)polymer A synthesized from at least one cationic monomer and at least one anionic monomer with preferably an overall cationic charge, with an inverse EMI 2 emulsion comprising a cross-linked water-soluble (co)polymer B synthesized from at least one cationic monomer. The water-soluble (co)polymers A and B are preferably different from each other.

In one preferred embodiment, concerning any kind of addition, the method of the invention further comprises a subsequent step of concentration, advantageously by distillation, of inverse EMI 1 emulsion. This concentration step consists of eliminating at least some water and/or oil from EMI 1 emulsion.

Thus, one preferred embodiment of the invention relates to a method for preparing a distilled inverse EMI 3 emulsion comprising the following steps:

a) Preparation of an inverse EMI 1 emulsion comprising mixing an aqueous solution comprising a water-soluble (co)polymer A synthesized from at least one cationic monomer, with an inverse EMI 2 emulsion comprising a water-soluble (co)polymer B synthesized from at least one cationic monomer, water-soluble (co)polymers A and B are preferably different from each other.

b) Distillation of the inverse EMI 1 emulsion to obtain an inverse EMI 3 emulsion.

Distillation means a partial removal of water from the hydrophilic phase and/or of the oil of the emulsion formed by the mixture of water-soluble (co)polymers A and B. As a technique for removing water, we can mention as an example distillation under reduced pressure. This distillation may be continuous or discontinuous, with azeotropic entrainment. Preferably, the distillation is continuous, and a light oil (boiling point below 200° C.) is advantageously used (EMI 2) to facilitate the entrainment of the water.

Advantageously, the formation of the EMI 3 emulsion does not require additional oil since the oil of the EMI 3 emulsion comes from the EMI 2 emulsion. Inverse EMI 3 emulsions obtained after distillation are thus concentrated in (co) polymers A and B. Inverse EMI 3 emulsions are obtained, the concentration of (co)polymers A and B of which may be between 20 and 80% by weight. Preferably, the mass concentration of (co)polymers A and B, after distillation, is between 30 and 70% by weight, even more preferentially between 35 and 60% by weight, relative to the mass of the EMI 3 emulsion.

One particular embodiment of the invention relates to a process for preparing a distilled reverse EMI 3 emulsion comprising the following steps:

a) Preparation of an inverse EMI 1 emulsion comprising mixing an aqueous solution comprising a water-soluble (co)polymer A synthesized from at least one cationic monomer and at least one anionic monomer, preferably with an overall cationic charge with an inverse EMI 2 emulsion comprising a cross-linked water-soluble (co)polymer B synthesized from at least one cationic monomer, the water-soluble (co)polymers A and B are preferably different from each other.

b) Distillation of the inverse EMI 1 emulsion to obtain an inverse EMI 3 emulsion.

The mixing conditions must be such that the inverse EMI 1 emulsion is not inverted or destabilized during mixing. A person skilled in the art will know how to adjust these parameters to comply with this condition.

All the preferences associated with water-soluble (co) polymers A and B described above may be added and combined with the process for obtaining the inverse EMI 1 emulsion or EMI 3 according to the invention.

Uses and Advantages of Inverse EMI 1 Emulsion and Inverse EMI 3 Emulsion Obtained According to the Process of the Invention Another subject-matter of the invention relates to a detergent, cosmetic, or fabric softening composition comprising an inverse EMI 1 emulsion or inverse EMI 3 emulsion obtained according to the process of the invention. The EMI 1 emulsion consists of mixing an aqueous solution comprising water-soluble (co)polymer A of at least one cationic monomer, with an inverse EMI 2 emulsion comprising a water-soluble (co)polymer B of at least one cationic monomer. EMI 3 emulsion generally corresponds to EMI 1 emulsion after a distillation step.

Preferably, the detergent or cosmetic or fabric softener composition is a fabric softener composition. It includes EMI 1 emulsion or EMI 3 emulsion in inverted form.

A fabric softener composition is a liquid composition added during the rinse cycle in a washing machine to make clothing more comfortable to the touch. These products work by depositing conditioning agents (quaternized esters, cationic polymers, etc.) on the fabric, making it softer and reducing static cling.

Typically, a fabric softener composition includes conditioning agents and surfactants. Surfactants particularly preferred for fabric softening compositions are certain nonionic surfactants, such as fatty acid esters of monoalcohols and polyalcohols, for example, glycerol monostearate, sorbitan monolaurate, and sorbitan monooleate.

In addition to these conditioning agents and surfactants, fabric softener compositions may contain other ingredients to enhance their aesthetic appeal and ensure product preservation. For example, fragrance or color may be added to make the product more pleasing to consumers. In addition, preservatives are often used to ensure product quality and preservation.

The softening composition according to the invention remains conventional as far as the general knowledge of a person skilled in the art is concerned. The latter will be able to adapt the concentrations of the various components and the various parameters to achieve the manufacture of the softening composition.

Preferably, the amount of active ingredient (sum of water-soluble (co)polymers A and B) used for softening compositions is between 0.01% and 1% by weight, more preferably between 0.1 and 0.5% by weight, with respect to the total mass the composition.

Another subject-matter of the invention relates to the use of an inverse EMI 1 emulsion or 3 obtained by the process according to the invention for improving the softening properties of a fabric softening composition.

Inverse EMI 1 or 3 emulsions obtained according to the process of the invention make it possible to obtain a combination of stable ionic (co)polymers (cationic and optionally anionic fillers) as well as ease of use and incorporation of these (co)polymers during the manufacture of detergent or cosmetic or fabric softener compositions.

In addition to the above advantages, the (co)polymers included in the EMI 1 or inverse EMI 3 emulsions obtained according to the process of the invention offer better softening performance than if they were used and added separately in detergent compositions. or cosmetics.

The process according to the invention is not limited to the field of detergents and cosmetics.

Applications to the method according to the invention may be found in any field where it is possible to envisage adding two products in one to facilitate use, in particular in industrialization.

The invention and the advantages thereof will become clearer from the following figures and examples given to illustrate the invention and not in a limiting manner.

FIGURES

EXAMPLES

Figure 1:
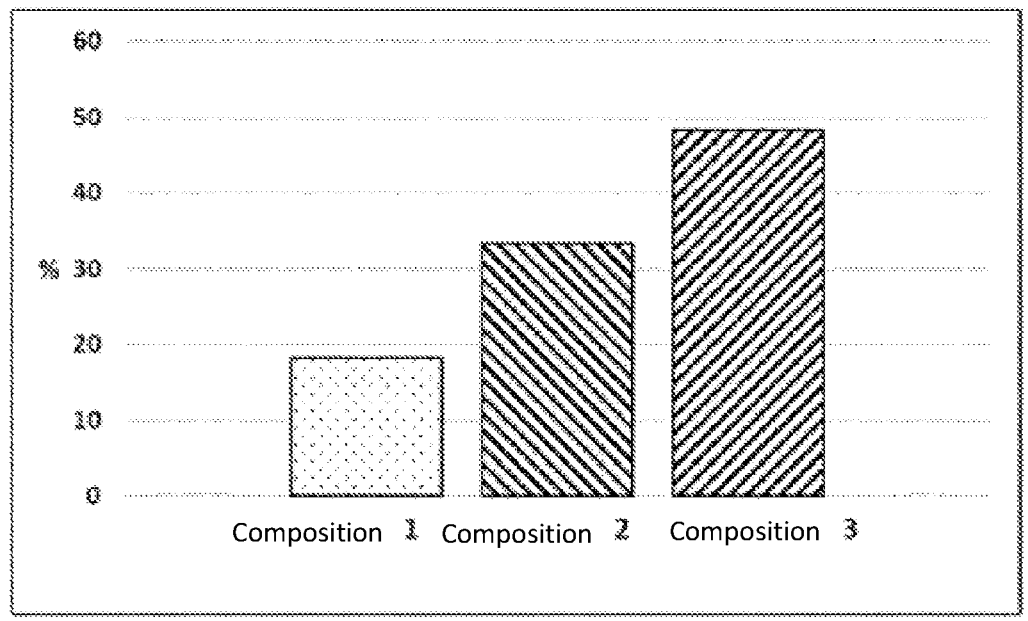
FIG. 1 is a graph showing the panel test results after one wash, between a separate addition of copolymers 1 and 3 to the composition and the addition of the emulsion according to the process of the invention (with and without the distillation step).

DADMAC=Dimethyldiallylammonium chloride
AA=Acrylic Acid
ACM=Acrylamide
M-PEG2000=Methoxy polyethylene glycol 2000
MADAME=Dimethylaminoethyl methacrylate
A/ Preparation of Water-Soluble Copolymers A and B
Preparation of the Water-Soluble Copolymer a in the Form of an Aqueous Solution:

Copolymer DADMAC/Acrylamide (Polymer A-1)

Copolymer A-1 comprises 56.7% by weight of Acrylamide and 43.3% in bulk of DADMAC. In a reactor equipped with a mechanical stirring system, a condenser, a thermometer, and a nitrogen supply, the following are added:

89 g of Acrylamide (Flocryl Acrylamide 50% by weight in water, SNF);
53 g of DADMAC (Flocryl 4007 Q 64% by weight in water, SNF);
785 g of water.

The medium is deoxygenated with a stream of nitrogen and heated to 50° C.

Two solutions of initiators are prepared separately, which are then added to the medium:

Solution 1:1 g of sodium persulfate in 10 g of water.
Solution 2:1 g of sodium metabisulphite in 100 g of water.

The medium is maintained at this temperature for one hour to complete the polymerization.

The mixture is allowed to return to ambient temperature; then, the pH is adjusted to between 3.8 and 4.3 using an aqueous solution of NaOH or citric acid at 50% by weight.

The product obtained is an aqueous solution whose concentration of copolymer A-1 is 9.4% by weight relative to the mass of the solution. The solution has a viscosity of 9300 cPs (Brookfield RVT, module 4, 10 rpm, 25° C.). Copolymer A-1 has a mass average molecular weight of 1,400,000 g/mol.

Following the same protocol, different water-soluble copolymers (A-2 to A-5) were synthesized. All compositions of the different water-soluble copolymers A are given in the following table:

TABLE 1

Summary of the compositions of water-soluble copolymers A.

|  | ACM % | DADMAC % | AA % | M-PEG 2000% | Solution strength (% by weight of copolymer A) |
|---|---|---|---|---|---|
| Copolymer A-1 | 43.3 | 56.7 | — | — | 9.4% |
| Copolymer A-2 | — | 80 | 20 | — | 40.5% |
| Copolymer A-3 | 75 | 25 | — | — | 39.9% |
| Copolymer A-4 | 29 | 48 | 23 | — | 44% |
| Copolymer A-5 | 68.1 | 27.4 | — | 4.5 | 10.2% |

Preparation of the Water-Soluble Copolymer B in the Form of an Inverse EMI 2 Emulsion:

Copolymer MADAME/Acrylamide (Polymer B-1)

Copolymer B-1 comprises 92% in mass of MADAME/MeCl and 8% by weight of Acrylamide.

The ingredients of the aqueous phase are loaded into a 1 L beaker with magnetic stirring:

468 g of MADAME/MeCl (Flocryl MADAME/MeCl 75% by weight in water, SNF);
60 g of Acrylamide (Flocryl Acrylamide 50% by weight in water, SNF);
130 g of water;
0.191 g of methylenebisacrylamide;
0.08 g of sodium diethylenetriaminepentacetate (Versenex 80).

Then in a 1 L glass reactor, with mechanical stirring, the organic phase is prepared with:

206 g of white mineral oil;
64 g of aliphatic hydrocarbon;
20 g of sorbitol monooleate;
5 g of stabilizing polymer.

The aqueous phase is transferred to the organic phase. The pre-emulsion thus formed is then subjected to high shear for 1 minute (Ultra Turrax, IKA).

The inverse emulsion is then degassed for 30 minutes by simple nitrogen bubbling.

Polymerization is carried out by adding a redox couple of sodium metabisulfite and tert-butyl hydroperoxide in solution in water.

After having reached the maximum temperature (adiabatic polymerization), the emulsion is maintained at 65° C. for 1 hour.

The mixture is allowed to return to room temperature to obtain the inverse EMI 2 emulsion.

Inverse EMI 2 emulsion is an opaque liquid whose concentration of copolymer B-1 is 38% by weight relative to the mass of the emulsion. Inverse EMI 2 emulsion has a viscosity of 640 cPs (Brookfield LVT, module 3, 30 rpm).

B/ Preparation of the Inverse EMI 1 Emulsion According to the Invention

Mixing Protocol:

450 g of the inverse EMI 2 emulsion at room temperature are introduced into a 1 L beaker. While stirring (three-blade, 600 rpm), 50 g of copolymer A-2 is added and stirred for 15 minutes at 600 rpm.

The EMI 1 obtained is an opaque liquid whose total concentration of copolymer (A-2+B-1) is 38.3% by weight relative to the mass of the solution. The solution has a viscosity of 760 cPs (Brookfield LVT, modulus 3, 30 rpm, 25° C.).

The different inverse EMI 1 emulsions are produced with the same protocol from the water-soluble copolymers A synthesized previously.

For direct use (without distillation step), it is necessary to add an inverting surfactant. In this case, 60 g of ethoxylated tridecyl alcohol (6 moles) are therefore added.

C/ Preparation of the Inverse EMI 3 Emulsion According to the Invention

Distillation Protocol:

277 g of EMI 1 are introduced into a 1 L flask. The latter is distilled using a rotary evaporator with a bath at 90° C. with rotation at 60 rpm, lowering the pressure to 80 mbar.

After distillation, 176.82 g are obtained, then 10.61 g of ethoxylated tridecyl alcohol (6 moles) are added as an inverting agent in order to obtain the invert EMI 3 emulsion.

Different inverse EMI 3 emulsions are produced with the same protocol from the inverse EMI 1 emulsions prepared previously.

The product obtained is an opaque liquid with a total copolymer concentration (A-2+B-1) of 56.6% by weight in relation to the solution mass. This solution has a viscosity of 1920 cPs (Brookfield LVT, module 3, 30 rpm, 25° C.).

Viscosity Test:

The viscosity is measured using a Brookfield LVT viscometer, with a module 3 at 30 rpm, at 25° C. At identical concentrations, the viscosity of the solutions of water-soluble copolymers A is greater than those of water-soluble copolymers B and, therefore, the most troublesome during the manufacture of compositions. Also, the viscosity of the aqueous solutions of copolymers A is compared to the viscosity of the inverse emulsions EMI 1 obtained according to the invention to assess the effectiveness of the process according to the invention for reducing viscosity without altering the properties of the copolymers.

The viscosities of the inverse EMI 3 emulsions obtained according to the invention are also measured (Table 2).

form a 2 in 1 product) to a composition. This effect is further increased due to the distillation step.

Softness Panel Tests:

Softness tests (softening effect) have been carried out by an independent laboratory.

Using a sensory panel (semi-trained), this method makes it possible to understand the softness provided by the product to the cotton textile. Towels are machine washed at 60° C.

After a cycle (wash+softening), the towels are left to dry in the open air on a household drying rack overnight in an air-conditioned room, then judged by a panel of 20 people. At the end of the panel, the towels are washed 4 times in a row (washing+softening+drying) and extended as described previously in order to perform the $2^{nd}$ panel after 5 iterative washes (5 wash cycles+softening+drying).

Statistical processing of the results is carried out to conclude the significance of the observed differences.

If the number of products to be tested is greater than three, then the ISO 8587 standard is applied. For two or three products, the ISO 5495 standard is used for data processing.

TABLE 2

Summary of Viscosities.

| Copolymer | Viscosity of aqueous solutions of copolymers A (cPs) | Viscosity Emulsions EMI 1 (cPs) | Viscosity reduction (%) | Viscosity Emulsions EMI 3 (cPs) | Viscosity reduction (%) | Mass ratio B-1/A |
|---|---|---|---|---|---|---|
| A-1 | 9300 | 640 | 93 | 1500 | 83 | 8.89 |
| A-2 | 6500 | 760 | 89 | 1920 | 70 | 8.55 |
| A-3 | 5000 | 1160 | 76 | 2960 | 40 | 6.4 |
| A-4 | 2800 | 936 | 66 | 1480 | 47 | 7.0 |
| A-5 | 8500 | 5800 | 31 | 1880 | 77 | 11.2 |

The process, according to the invention, makes it possible to obtain stable inverse emulsions of copolymers which, if added separately, are generally incompatible.

Besides this compatibility, the viscosity of the mixture is significantly lower than that of the copolymer in solution, with a reduced viscosity between 40% and 83% after distillation.

This reduction in viscosity is even greater without the distillation step, with a reduction ranging from 66% to 91%.

This significant reduction in viscosity simplifies the use of copolymers A and B during processes for formulating detergent or cosmetic compositions, in particular for decanting, storage, and metering stages.

Thanks to the invention and the 2-in-1 addition of these copolymers, there is also a space increase in the installations and a reduction in logistics.

The energy used to pump the products is also much lower in the context of the invention and allows a reduction in the ecological footprint.

In addition to all these advantages, it has been surprisingly discovered that the softening effect of the mixture of the copolymers obtained according to the process of the invention is increased compared to the effect obtained when the copolymers are added separately (the copolymers do not Mixing Protocol:

Method for separately adding the water-soluble co-polymers A and B:

While stirring, the inverse EMI 2 emulsion, comprising the water-soluble copolymer B, is added to the Minidou® softening composition, Breath of Fresh Air. The mixture continues to be stirred for 15 minutes before adding the aqueous solution A of water-soluble copolymers A. This entire amount continues to be stirred for 15 minutes.

The compositions below are thus obtained:

Composition 1: The aqueous solution of copolymers A-1 and the inverse EMI 2 emulsion are added separately.

Composition 2: Inverse EMI 1 emulsion of water-soluble copolymers A-1 and B-1 according to the invention.

Composition 3: Inverse EMI 3 emulsion of water-soluble copolymers A-1 and B-1 according to the invention.

Composition 4: The aqueous solution of copolymers A-2 and the inverse EMI 2 emulsion are added separately.

Composition 5: Inverse EMI 1 emulsion of water-soluble copolymers A-2 and B-1 according to the invention.

Composition 6: Inverse EMI 3 emulsion of water-soluble copolymers A-2 and B-1 according to the invention.

Results of the Softness Panel Tests for Compositions 1 to 3:

TABLE 3

Figure 2:
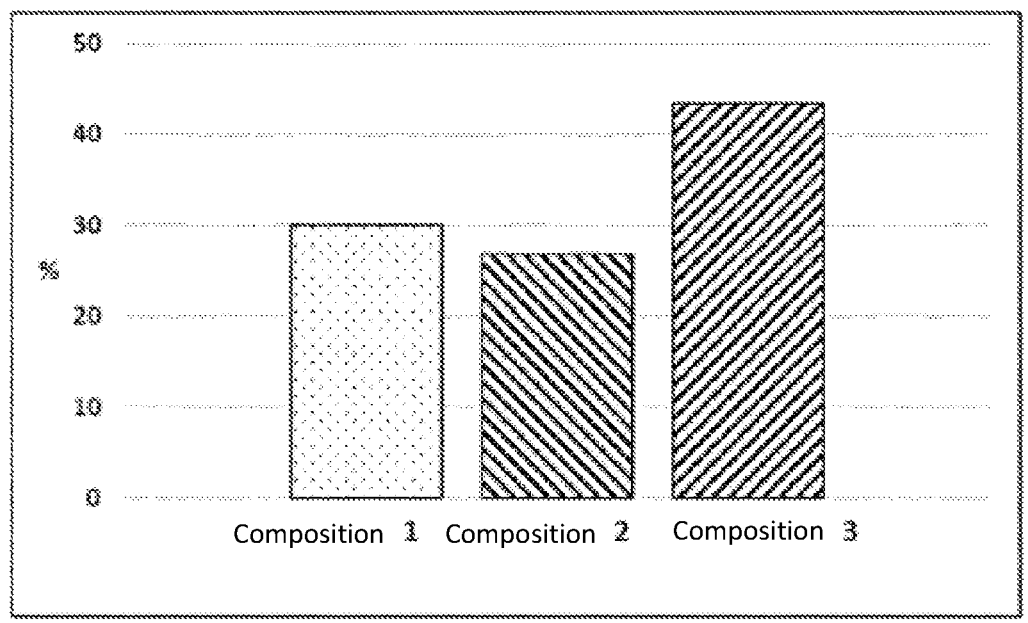
FIG. 2 is a graph showing the panel test results after five washes, between a separate addition of copolymers 1 and 3 to the composition and the addition of the emulsion according to the process of the invention (with and without the distillation step).

Distribution (percentage, %) of the panel choices during the softness test after 1 and 5 washes with compositions 1 to 3 (FIGS. 1 and 2).

|  | % of people who chose Composition 1 | % of people who chose Composition 2 | % of people who chose Composition 3 |
|---|---|---|---|
| 1 Wash | 18.3 | 33.3 | 48.3 |
| 5 Wash | 30.0 | 26.7 | 43.3 |

Compositions 2 and 3, obtained according to the process of the invention, represent 81.6% of the panel's choices for their softness preference after a single wash.

The distillation step reinforces this softening effect, with almost half of the panelists choosing towels washed with composition 3.

Compositions comprising the copolymers obtained according to the process of the invention represent 70% of the panel's choices for their softness preference after 5 washes.

After the distillation step, the soft side of the towel was again reinforced, with almost 45% of the participants selecting composition 3.

Results of the Softness Panel Tests for Compositions 4 to 6:

TABLE 4

Figure 3:
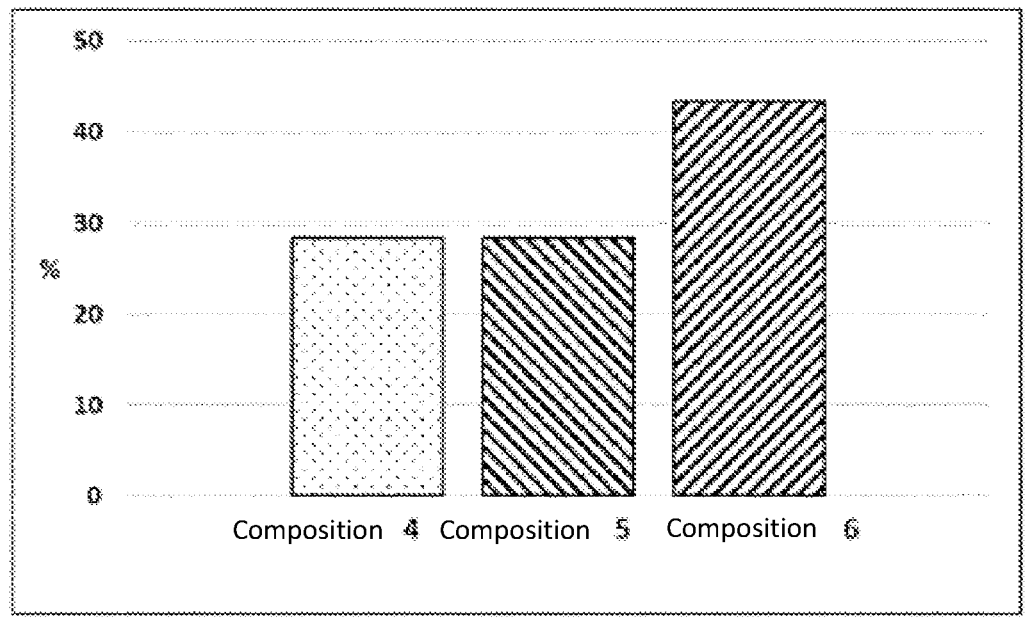
FIG. 3 is a graph showing the panel test results after one wash, between a separate addition of copolymers 2 and 3 to the composition and the addition of the emulsion according to the process of the invention (with and without the distillation step).
Figure 4:
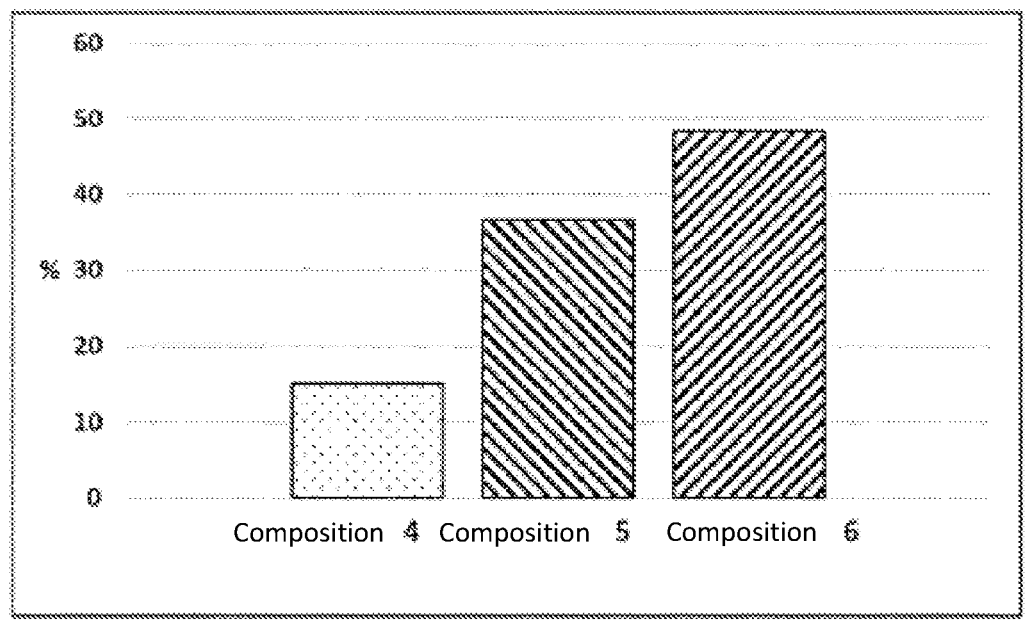
FIG. 4 is a graph showing the panel test results after one wash, between a separate addition of copolymers 2 and 3 to the composition and the addition of the emulsion according to the process of the invention (with and without the distillation step).

Distribution of panel choices during the softness test after 1 and 5 washes for compositions 4 to 6 (FIGS. 3 and 4).

|  | % of people who chose Composition 4 | % of people who chose Composition 5 | % of people who chose Composition 6 |
|---|---|---|---|
| 1 Wash | 28.3 | 28.3 | 43.3 |
| 5 Wash | 15.0 | 36.7 | 48.3 |

Compositions 5 and 6 comprising the copolymers obtained according to the process of the invention represent 71.6% of the panel's choices for their softness preference after a single wash. The distillation step reinforces this softening effect, with almost 45% of the panelists choosing towels washed with composition 6.

Compositions comprising the copolymers obtained according to the process of the invention represent 85% of the panel's choices for their softness preference after 5 washes.

The distillation step reinforces this softening effect, with almost half of the panelists choosing towels washed with composition 3.

Towel Fluffiness Test:

An important aspect for the consumer is the fluffiness of the towels. This is measured by taking the stack height of 20 towels. The measurement is taken before washing, after a first wash, and after 5 washes in order to compare the softness of the towels.

TABLE 5

Figure 5:
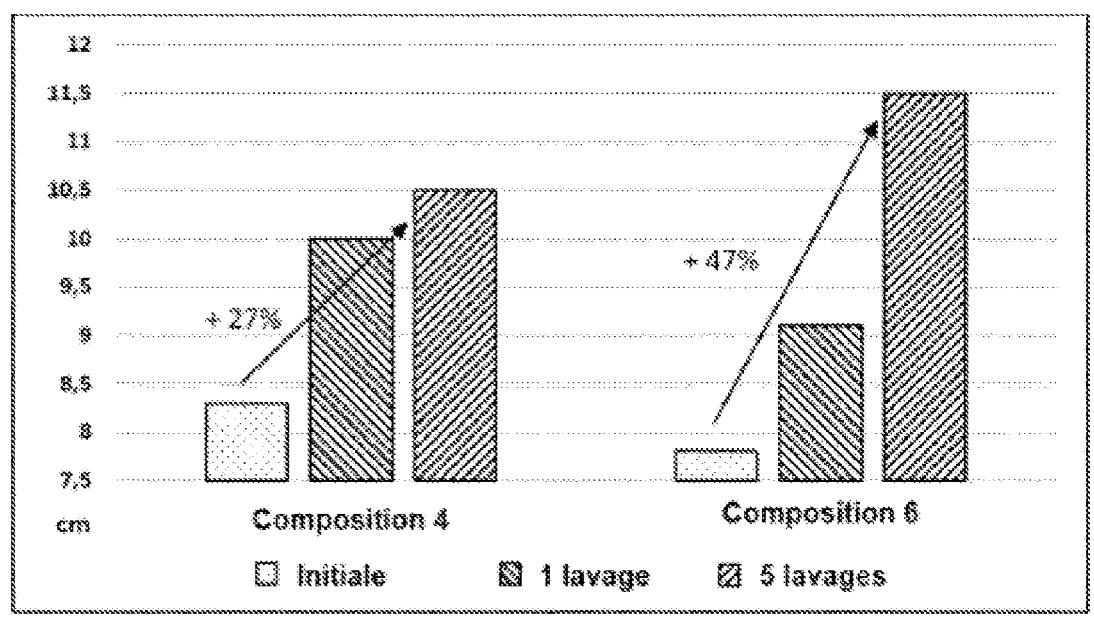
FIG. 5 is a graph showing the softening effect the emulsions according to the process of the invention have on towels.

Comparison of the measurement of the stack height of 20 towels washed with a separate addition and the copolymers obtained according to the process of the invention (FIG. 5).

|  | Composition | Improvement | Composition 6 | Improvement |
|---|---|---|---|---|
| Before washing |  | 28.3 | 28.3 |  | 43.3 |
| 1 Wash |  | 15.0 | 36.7 |  | 48.3 |
| 5 Washes |  |  |  |  |  |

It may be seen that the increase in thickness is greater for the composition comprising the inverse emulsion obtained according to the invention, with an increase of almost 50% in stack height after 5 washes. By adding the water-soluble copolymers A and B separately, the increase is only 27%. The increase in thickness is doubled thanks to the method according to the invention.

Successive washes improve the softening effect due to an improved deposition of the softening copolymers.

D/ Viscosity Reduction

The inverse emulsion, according to the invention, EMI 1 and EMI 3, was compared to an emulsion resulting from the formation of copolymer A by polymerization of monomers in the presence of copolymer B-1 (comparative process CE).

The CE comparative process is similar to that described in documents EP 0 262 945, U.S. Pat. No. 8,633,278 or US 2002/0188040.

Table 6 compares the viscosity of the emulsions according to the invention and according to the CE comparative process before and after distillation.

TABLE 6

Comparison of the viscosity of the emulsions obtained according to the process of the invention or according to the CE comparative process.

| Copolymer | Process | Viscosity (cPs) before distillation | Viscosity (cPs) after distillation | Mass ratio B-1/A |
|---|---|---|---|---|
| A-1 | Invention | 640 (EMI 1) | 2400 (EMI 3) | 11.8 |
|  | CE | 760 (CE-1) | 3080 (CE-1dist) | 29.4 |
| A-2 | Invention | 640 (EMI 1) | 2400 (EMI 3) | 6.1 |
|  | CE | 1240 (CE-2) | 3720 (CE-2dist) | 6.7 |

Copolymer A-1 is a copolymer of 43.3% by weight ACM (acrylamide) and 56.7% by weight DADMAC (dimethyldiallylammonium chloride). Copolymer B-1 is a copolymer of 92% by weight of MADAME/MeCl (Dimethylaminoethyl methacrylate quaternized with methyl chloride) and 8% by weight of ACM. At identical concentrations, the viscosity of the solutions of water-soluble copolymers A is greater than those of water-soluble copolymers B and, therefore, the most troublesome during the compositions' preparation.

The EMI 1 and EMI 3 emulsions were prepared according to sections B/ and C/ above.

The CE process consists of preparing emulsions CE-1 and CE-2 by polymerization, in inverse emulsion, of 43.3% by weight of ACM and 56.7% by weight of DADMAC (dimethyldiallylammonium chloride) in the presence of copolymer B-1. Emulsions CE-1dist and CE-2dist were prepared according to the distillation protocol of section C/ above.

According to the data in Table 6, the inverse emulsion obtained according to the invention (EMI 1 or EMI 3) has a viscosity (640 or 2400 cps) lower than that of the composition according to the CE comparative process (760 or 3080 cps) and this, even if it has a copolymer mass ratio B-1/copolymere A more important (11.8 vs. 29.4). It is thus possible, thanks to the invention, to increase the concentration of copolymer without causing any viscosity problem.

On the other hand, at a similar copolymer ratio (ratio B-1/A=6.1 or 6.7), the viscosity of the inverse emulsion according to the invention (640 or 2400 cps) is markedly lower than that of a composition according to the comparative CE (1240 or 3720 cps) process.

Thus, these tests show that the process according to the invention makes it possible to solve the problem linked to the manipulation of viscous polymers.

Indeed, the preparation of an inverse emulsion according to the process of the invention makes it possible, with a constant quantity of polymer, to reduce the viscosity and, therefore, to facilitate the use of copolymers with viscosifying properties.

The invention claimed is:

1. A process for preparing an inverse EMI 1 emulsion comprising the following step:
    forming an inverse EMI 1 emulsion by mixing an aqueous solution of water-soluble (co)polymer A of at least one cationic monomer and an inverse EMI 2 emulsion of water-soluble (co)polymer B of at least one cationic monomer.

2. The process for the preparation of an inverse emulsion according to claim 1, wherein water-soluble (co)polymers A and B are synthetic (co)polymers obtained, independently of each other, from at least one cationic monomer and at least one non-ionic monomer and/or of at least one anionic monomer.

3. The process for the preparation of an inverse emulsion according to claim 1, wherein water-soluble (co)polymers A and B are, independently of each other, synthetic (co)polymers of at least one cationic monomer selected from quaternized dimethylaminoethyl acrylate (ADAME), quaternized dimethylaminoethyl methacrylate (MADAME), dimethyldiallylammonium chloride (DADMAC), acrylamido propyltrimethyl ammonium chloride (APTAC), methacrylamido propyltrimethyl ammonium chloride (MAPTAC), and mixtures thereof.

4. The process for the preparation of an inverse emulsion according to claim 1, wherein water-soluble (co)polymer A and water-soluble (co)polymer B are, independently of each other, (co)polymers:
    of at least one cationic monomer, and
    of at least one non-ionic monomer and/or at least one anionic monomer, the non-ionic monomer being chosen from acrylamide, methacrylamide, N-isopropylacrylamide, N,N-dimethylacrylamide and N-methylolacrylamide, N-vinylformamide, N-vinyl acetamide, N-vinylpyridine and N-vinylpyrrolidone, acryloyl morpholine (ACMO), diacetone acrylamide, and mixtures thereof.

5. The process for the preparation of an inverse emulsion according to claim 1, wherein water-soluble (co)polymer A and water-soluble (co)polymer B are, independently of each other, (co)polymers:
    of at least one cationic monomer, and
    of at least one anionic monomer and/or at least one non-ionic monomer the anionic monomer chosen from acrylic acid, methacrylic acid, itaconic acid, maleic acid, 2-acrylamido-2-methylpropane sulfonic acid (ATBS), vinylsulfonic acid, vinylphosphonic acid and mixtures thereof, said anionic monomer being non-salified, partially or totally salified, and the salts of 3-sulfopropyl methacrylate.

6. The process for the preparation of an inverse emulsion according to claim 1, wherein water-soluble (co)polymer A is a water-soluble (co)polymer synthesized from at least one cationic monomer and from at least one anionic monomer, water-soluble (co)polymer A having an overall cationic charge.

7. The process for the preparation of an inverse emulsion according to claim 1, wherein water-soluble (co)polymer B is a cross-linked water-soluble (co)polymer.

8. The process for the preparation of an inverse emulsion according to claim 1, wherein the inverse EMI 1 emulsion comprises a total concentration of water-soluble (co)polymers A and B of between 5 and 50% weight relative to the total weight of the inverse EMI 1 emulsion.

9. The process for the preparation of an inverse emulsion according to claim 1, wherein the process comprises a subsequent step of forming an inverse EMI 3 emulsion by distillation of the inverse EMI 1 emulsion.

10. The process for the preparation of an inverse emulsion according to claim 1, wherein the process comprises a subsequent step of forming an inverse EMI 3 emulsion by distillation of the inverse EMI 1 emulsion, the inverse EMI 3 emulsion with a total concentration of water-soluble (co)polymers A and B of between 20 and 80% by weight relative to the total weight of the inverse EMI 3 emulsion.

11. The process for the preparation of an inverse emulsion according to claim 1, wherein the process comprises a subsequent step of forming an inverse EMI 3 emulsion by distillation of the inverse EMI 1 emulsion, the inverse EMI 3 emulsion having a total concentration of water-soluble (co)polymers A and B of between 35 and 60% by weight relative to the total weight of the inverse EMI 3 emulsion.

12. The process for the preparation of an inverse emulsion according to claim 11, wherein the inverse EMI 1 or EMI 3 emulsion has a mass ratio between the water-soluble (co)polymer B and water-soluble (co)polymer A between 1 and 100.

13. The process for the preparation of an inverse emulsion according to claim 6, wherein water-soluble (co)polymer B is a cross-linked water-soluble (co)polymer.

14. The process for the preparation of an inverse emulsion according to claim 2, wherein:
    the at least one cationic monomer is selected from quaternized dimethylaminoethyl acrylate (ADAME), quaternized dimethylaminoethyl methacrylate (MADAME), dimethyldiallylammonium chloride (DADMAC), acrylamido propyltrimethyl ammonium chloride (APTAC), methacrylamido propyltrimethyl ammonium chloride (MAPTAC), and mixtures thereof;
    the at least one non-ionic monomer is selected from acrylamide, methacrylamide, N-isopropylacrylamide, N,N-dimethylacrylamide and N-methylolacrylamide, N-vinylformamide, N-vinyl acetamide, N-vinylpyridine and N-vinylpyrrolidone, acryloyl morpholine (ACMO), diacetone acrylamide, and mixtures thereof; and
    the at least one anionic monomer is selected from acrylic acid, methacrylic acid, itaconic acid, maleic acid, 2-acrylamido-2-methylpropane sulfonic acid (ATBS), vinylsulfonic acid, vinylphosphonic acid and mixtures thereof, said anionic monomer being non-salified, partially or totally salified, and the salts of 3-sulfopropyl methacrylate.

15. The process for the preparation of an inverse emulsion according to claim 14, wherein water-soluble (co)polymer A is a water-soluble (co)polymer synthesized from at least one cationic monomer and from at least one anionic monomer, water-soluble (co)polymer A having an overall cationic charge.

16. The process for the preparation of an inverse emulsion according to claim 5, wherein water-soluble (co)polymer B is a cross-linked water-soluble (co)polymer.

17. The process for the preparation of an inverse emulsion according to claim 16, wherein:
- the inverse EMI 1 emulsion comprises a total concentration of water-soluble (co)polymers A and B of between 5 and 50% weight relative to the total weight of the inverse EMI 1 emulsion;
- the process comprises a subsequent step of forming an inverse EMI 3 emulsion by distillation of the inverse EMI 1 emulsion, the inverse EMI 3 emulsion with a total concentration of water-soluble (co)polymers A and B of between 35 and 60% by weight relative to the total weight of the inverse EMI 3 emulsion; and
- the inverse EMI 1 or EMI 3 emulsion has a mass ratio between the water-soluble (co)polymer B and water-soluble (co)polymer A between 5 and 14.

\* \* \* \* \*

UNITED STATES PATENT AND TRADEMARK OFFICE
CERTIFICATE OF CORRECTION

PATENT NO. : 11,634,664 B2
APPLICATION NO. : 17/754891
DATED : April 25, 2023
INVENTOR(S) : Besset et al.

It is certified that error appears in the above-identified patent and that said Letters Patent is hereby corrected as shown below:

On the Title Page

In the PCT No. (86): Delete "PCT/US2020/079870" and insert -- PCT/EP2020/079870 --

In the Claims

Column 23 Line 6: Claim 16, Delete "claim 5" and insert -- claim 15 --

Signed and Sealed this
Twentieth Day of June, 2023

Katherine Kelly Vidal
*Director of the United States Patent and Trademark Office*